United States Patent
Baldessarini et al.

(10) Patent No.: US 6,221,883 B1
(45) Date of Patent: Apr. 24, 2001

(54) METHOD OF DOPAMINE INHIBITION USING L-THREO-METHYLPHENIDATE

(76) Inventors: Ross Baldessarini, 49 Nehoiden Rd., Newton, MA (US) 02468; Alexander Campbell, 51 Boxborough Rd., Littleton, MA (US) 02460

(*) Notice: Subject to any disclaimer, the term of this patent is extended or adjusted under 35 U.S.C. 154(b) by 0 days.

(21) Appl. No.: 09/547,767

(22) Filed: Apr. 12, 2000

(51) Int. Cl.$^7$ ................................. A61K 31/445
(52) U.S. Cl. .......................................... 514/317
(58) Field of Search ............................. 514/317

(56) References Cited

U.S. PATENT DOCUMENTS

| | | | |
|---|---|---|---|
| 5,874,090 | 2/1999 | Baker et al. | 424/400 |
| 5,908,850 | 6/1999 | Zeitlin et al. | 514/315 |

OTHER PUBLICATIONS

Aoyama et al., "Stereospecific distribution of methylphenidate enantiomers in rat brain: Specific binding to dopamine reuptake sites," *Pharm. Res.* 11:407–411 (1994).

Aoyama et al., "Pharmacokinetics and pharmacodynamics of methylphenidate enantiomers in rats," *Psychopharmacology* 127:117–122 (1996).

Breese et al., "Involvement of brain monoamines in the stimulant and paradoxical inhibitory effects of methylphenidate," *Psychopharmacologia(Berl)* 44:5–10 (1975).

Ding et al., "Chiral drugs: Comparison of the pharmacokinetics of [$^{11}$C]d–threo and l–threo–methylphenidate in the human and baboon brain," *Psychopharmacology* 131:71–78 (1997).

Eckerman et al., "Enantioselective behavioral effects of threo–methylphenidate in rats," *Pharmacology, Biochemistry & Behavior* 40(4):875–880 (1991).

Ferris et al., "Comparison of the effects of the isomers of amphetamine, methylphenidate and deoxypipradrol on the uptake of 1–[$^3$H] norepinephrine and [$^3$H]dopamine by synaptic vesicles from rat whole brain, striatum and hypothalamus," *J. Pharmacol. Exp. Ther.* 210(3):422–428 (1979).

Ferris et al., "A comparison of the capacities of isomers of amphetamine, deoxypipradrol and methylphenidate to inhibit the uptake of tritiated catecholamines into rat cerebral cortex slices, synaptosomal preparations of rat cerebral cortex, hypothalamus and striatum and into adrenergic nerves of rabbit aorta," *J. Pharmacol. Exp. Ther.* 181(3):407–416 (1972).

Froimowitz et al., "Conformational analysis of methylphenidate and its structural relationship to other dopamine reuptake blockers such as CFT," *Pharm. Res.* 12(10):1430–1434 (1995).

Janowsky et al., "The effects of surgical and chemical lesions on striatal [$^3$H] threo–(±)– methylphenidate binding: Correlation with [$^3$H] dopamine uptake," *Eur. J. Pharmacol.* 108:187–191 (1985).

Jonkman et al., "Differences in plasma concentrations of the D– and L–threo methylphenidate enantiomers in responding and non–responding children with attention–deficit hyperactivity disorder," *Psych. Res.* 78(1–2):115–118 (1998).

Leith et al., "Self–stimulation and amphetamine: tolerance to d and l isomers and cross tolerance to cocaine and methylphenidate," *Psychopharmacology* 74(1):23–28 (1981).

Maxwell et al., "Conformational similarities between molecular models of phenethylamine and of potent inhibitors of the uptake of tritiated norepinephrine by adrenergic nerves in rabbit aorta," *J. Pharmacol. Exp. Ther.* 173:158–165 (1970).

Navia et al., "The AIDS dementia complex: I. Clinical Features," *Ann. Neurol.* 19:517–524 (1986).

Patrick et al., "Pharmacology of the Enantiomers of threo–Methylphenidate," *J. Pharmacol. Exp. Ther.* 241:152–158 (1987).

Schweri, "N–ethylmaleimide irreversibly inhibits the binding of [$^3$H]threo–(+–)methylphenidate to the stimulant recognition site," *Neuropharmacology* 29(10):901–908 (1990).

Srinivas et al., "Enantioselective pharmacokinetics and pharmacodynamics of dl–threo– methylphenidate in children with attention deficit hyperactivity disorder," *Clin. Pharmacol. Ther.* 52:561–568 (1992).

Srinivas et al., "Stereoselective disposition of methylphenidate in children with attention–deficit disorder," *J. Pharmacol. Exp. Ther.* 241(1):300–306 (1987).

*Primary Examiner*—William R. A. Jarvis
(74) *Attorney, Agent, or Firm*—Clark & Elbing LLP

(57) ABSTRACT

This invention provides methods of effecting dopamine inhibition in a mammal by administering to the mammal l-threo-MPH which is substantially free from d-threo-MPH. Also provided by the invention are methods of inhibiting the effects of a stimulant in a mammal by administering to the mammal l-threo-MPH which is substantially free from d-threo-MPH.

12 Claims, 4 Drawing Sheets

S,S-(−)-*threo*-Methylphenidate
(MW = 233.31)

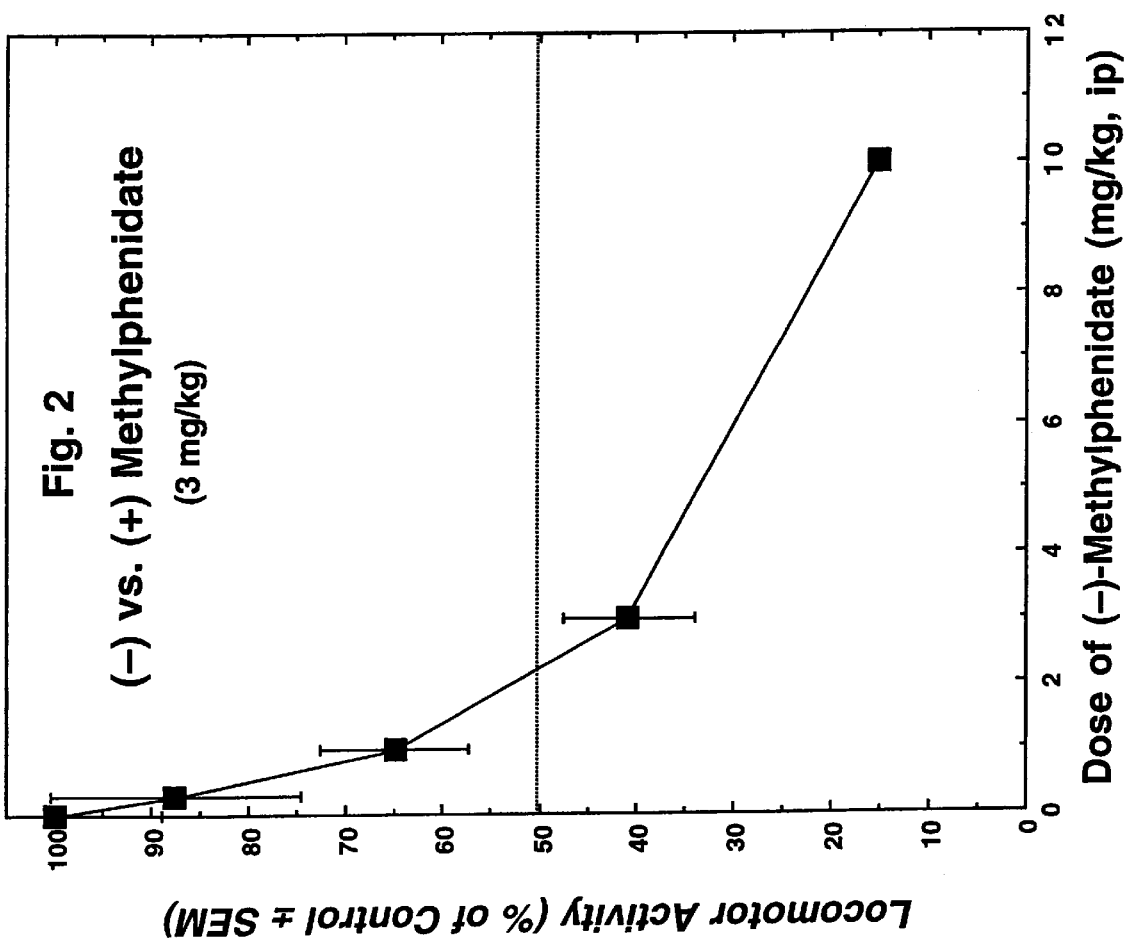

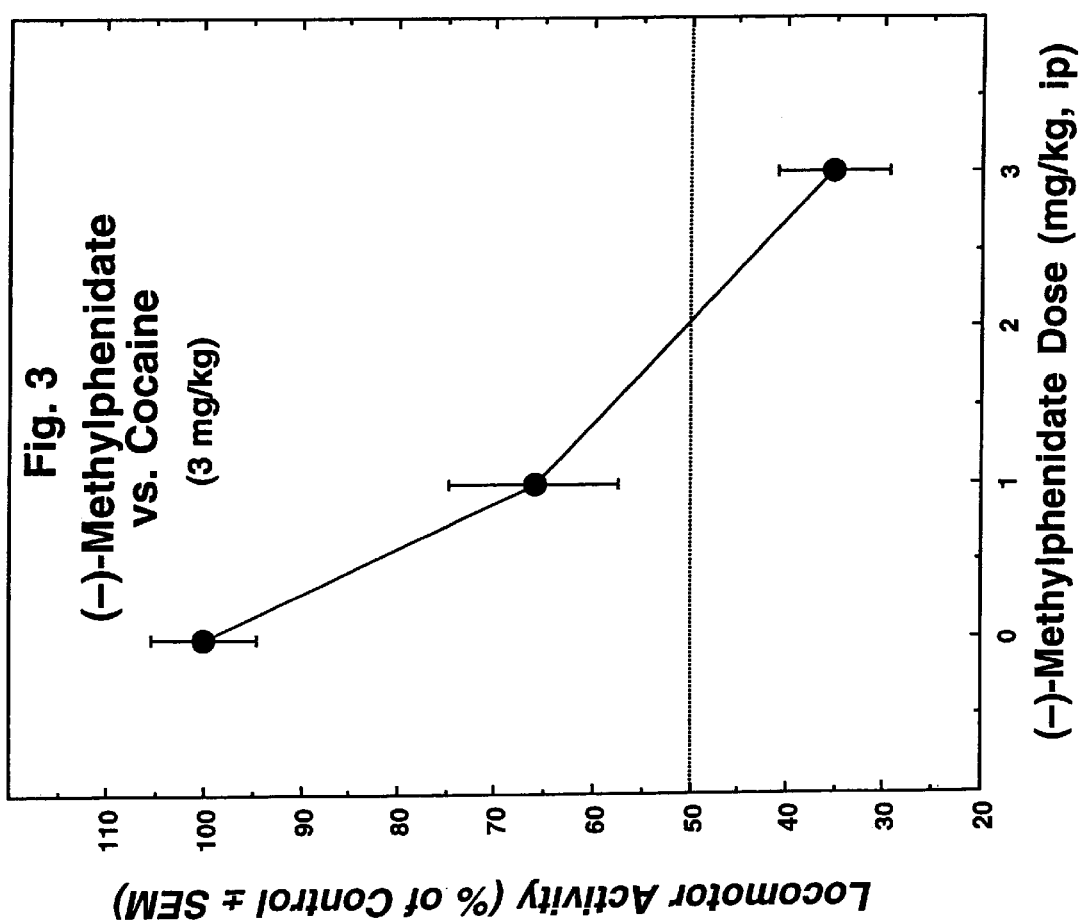

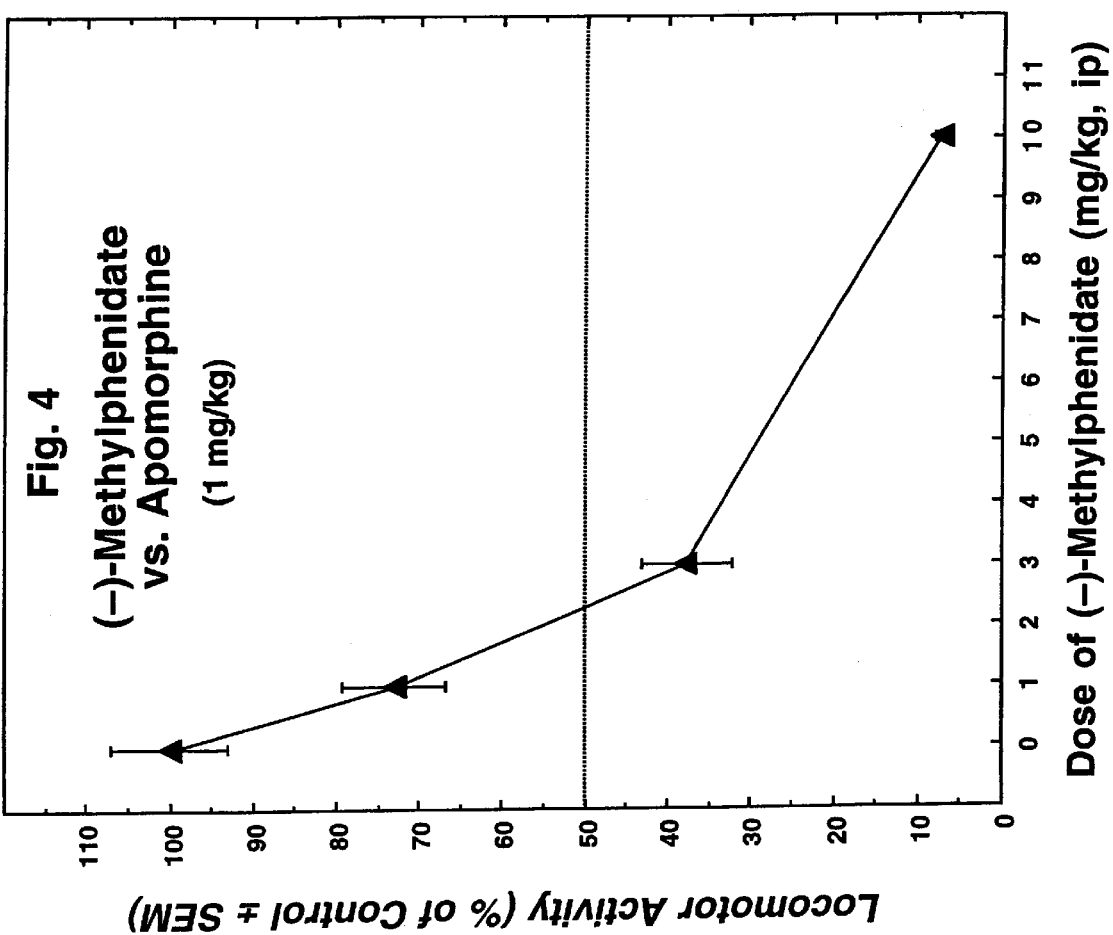

METHOD OF DOPAMINE INHIBITION USING L-THREO-METHYLPHENIDATE

STATEMENT AS TO FEDERALLY SPONSORED RESEARCH

The invention was funded, in part, by federal grants K05-MH-47370 and R-01-MH-34006. The government has certain rights in the invention.

BACKGROUND OF THE INVENTION

Racemic methylphenidate (MPH) is a central nervous system stimulant that has pharmacological activity qualitatively similar to amphetamines and is widely used in the treatment of attention deficit disorder (ADD) and attention-deficit hyperactivity disorder (ADHD) (l-threo isomer shown in FIG. 1). Symptoms of these disorders include distractability and impulsivity; ADHD is further associated with increased activity of the body. MPH has also been used to treat cognitive defects, including dementia, that manifest in at least 70% of HIV-infected individuals who have developed Acquired Immunodeficiency Syndrome (Navia et al. Ann. Neurol. 1986; 19:517–524). Additionally, d-threo-methylphenidate is used to treat hypersomnia (Aoyama et al. Clin. Pharmacol. Ther., 1994; 55:270–276)

Originally MPH was sold pharmaceutically as a mixture of two racemates, 80% dl-erthro and 20% dl-threo. Subsequent studies revealed that the central stimulant activity residues in the threo racemate, and thus the erythro racemate was removed from the pharmaceutical to improve its therapeutic index.

dl-threo-MPH appears to facilitate dopaminergic and noradrenergic transmission (Maxwell et al. J. Pharmacol. Exp. Ther. 1970;173:158–165; Breese et al., Paychopharmacology 1975; 44:5–10; Janowsky et al. Eur. J. Pharmacol. 1985; 108:187–191). Patrick et al. found that d-threo-MPH produced greater induction of locomotor activity in rats and greater inhibition of tritiated dopamine and l-norepinephrine uptake into striatal and hypothalamic synaptosomes, respectively, than the l-isomer (Patrick et al. J. Pharmacol. Exp. Therap. 1987; 241:152–158). Additionally, Srinivas et al. showed that the pharmacodynamic activity of the racemic threo-MPH in treating ADHD resides in the d-threo isomer (Srinivas et al. Clin. Pharmacol. Ther. 1992; 52:561–568). Administration of d-threo-MPH instead of dl-threo-MPH in patients suffering from ADD, ADHD, AIDS cognitive decline, and AIDS Dementia Complex resulted in less severe side effects. These include a reduction in the euphoric effect that is produced when dl-threo-MPH is administered intravenously or through inhalation, to create a potential for substance abuse in patients (U.S. Pat. No. 5,908,850). In rats, baboons, and humans, [$^{11}$C]d-threo-MPH demonstrated highest regional accumulation in the basal ganglia; in contrast, [$^{11}$C]d-threo-MPH displayed similar uptake in all brain regions, suggesting that its distribution in the brain is less specific. This result further supports the hypothesis that the pharmacological specificity of racemic threo-MPH in elevating striatal dopamine concentration resides in the d-threo isomer (Ding et al. Psychopharmacology 1997; 131:71–78; Aoyama et al. Pharm. Res. 1994; 11:407–411).

SUMMARY OF THE INVENTION

The invention features a method of effecting dopamine inhibition in a mammal, such as a human, by administering an effective inhibiting amount of l-threo-MPH which is substantially free from d-threo-MPH. This method can be used for the treatment or prevention of a manic disorder, a psychotic disorder, or an anxiety disorder.

In a related aspect, the invention further includes a method of inhibiting the effect of a stimulant by administering to a mammal l-threo-MPH which is free from d-threo-MPH to a mammal. Stimulants that can be inhibited according to the invention include cocaine, amphetamines, caffeine, and d-threo-MPH. The methods of the invention can also be used for treating or preventing the toxic effects of an overdose of a stimulant. By "effect of a stimulant" is meant induction of dopamine or l-norepinephrine uptake, distractibitlity, impulsivity, or hyperactivity.

l-threo-MPH is administered orally, intramuscularly, intravenously, or subcutaneously to the mammal. l-threo-MPH generally is administered together with a pharmaceutically acceptable carrier. Generally, dosage is in the same range as the dosage currently used for d-threo-MPH.

BRIEF DESCRIPTION OF THE DRAWINGS

FIG. 2 is a graph that shows the inhibition by l-threo-MPH of locomotor behavioral arousal in rates (N=6/dos of l-threo-MPH) treated with a fixed dose of d-threo-MPH [3 mg/kg, intraperitoneally (i.p.)]. The $ID_{50}$ of l-threo-MPH is approximately 2.5 mg/kg, i.p.

FIG. 3 is a graph that shows the inhibition by l-threo-MPH of locomotor behavioral arousal in rats (N=6/dose) treated with a fixed dose of the stimulant cocaine-HCl (3 mg/kg, i.p.). The $ID_{50}$ of by l-threo-MPH is approximately 2.0 mg/kg, i.p.

FIG. 4 is a graph that shows the inhibition by l-threo-MPH of locomotor behavior arousal in rats (N=6/dose) compared to a fixed dose of the direct dopamine agonist R(−)-apomorphine-HCl (1 mg/kg, i.p.). The $ID_{50}$ of l-threo-MPH is approximately 2.5 mg/kg, i.p.

DETAILED DESCRIPTION

Figure 1:
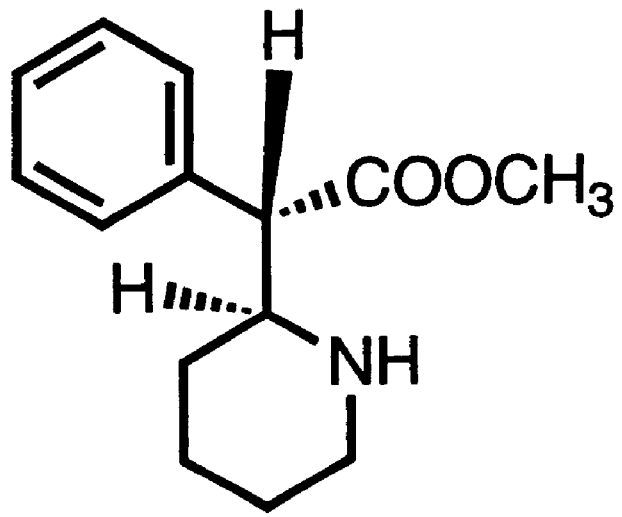
FIG. 1 is the structure of l-threo-MPH [(S,S(−)-threo-methylphenidate].

We have found that the d-threo-isomer of MPH is more than twice as potent as the clinically used dl-racemic mixture. We believe that the l-isomer interacts antagonistically with the pharmacologically active d-isomer. This novel finding was supported by the reduction in spontaneous locomotion in rats treated with d-threo-MPH after administration of l-threo-MPH (FIG. 2).

l-threo-MPH was also shown to inhibit the stimulant effects of other indirect or direct dopamine agonists. Specifically, l-threo-MPH displayed potent, dos-dependent inhibition of locomotion in rats induced by a fixed dose of the stimulant, indirect dopamine agonist cocaine (FIG. 3) or the classic direct dopamine agonist R(−)-apomorphine (FIG. 4). The aforementioned findings indicate that l-threo-MPH acts as an antagonist of central nervous system dopaminergic activity. Accordingly, the invention features a method for the treatment or prevention of a manic disorder, a psychotic disorder, or an anxiety disorder in a mammal such as a human patient, by administering to the mammal a pharmaceutically effective amount of l-threo-MPH substantially free of the d-threo isomer. Additionally, the invention includes a method for inhibiting the effect of a stimulant by administering the substantially pure l-threo-MPH isomer to a mammal.

The following example is to illustrate the invention; it is not meant to limit the invention in any way.

Inhibition of Locomotor Activity by l-threo-MPH

Young adult albino rates (Charles River CD-VAF, 200–300 g body weight) were injected with test drug or vehicle, and tested singly in their home cages between 10:00 and 16:00 hours to minimize the effects of circadian variations in behavioral responses. Six rats were tested per condition and compared to 18 pooled controls. l-threo-MPH was tested at doses of 0, 0.3, 1.0, 3.0, and 10.00 mg/kg [0.429, 1.29, 4.29, 12.9, and 42.9 $\mu$mole/kg intraperitoneally (i.p.)] at a volume of 1.0 mg/kg, in physiological saline (150 mM NaCl in purified water) as the vehicle, in rats given fixed doses of the stimulant d-threo-MPH (3 mg/kg, i.p.), the timulant cocaine-HCl (3 mg/kg, i.p.), or the direct dopamine agonsit R(−)-apomorphine-HCl (1 mg/kg, i.p.). Locomotion, as an index of behavioral arousal, was recorded in a Stoelting 12-channel electronic activity monitor (Wood Dale, Ill.) controlled by an Apple Macintosh microcomputer. Sensors were placed in an electrically-shielded and grounded, sound-attenuated closure to minimize environmental artifacts, spaced at least 50 cm apart to prevent radiofrequency coupling, and adjusted to respond to locomotion selectively and exclude small movements such as grooming and chewing. Sensor responses were frequently recalibrated and standardized using a pendulum. Locomotor activity data were accumulated and analyzed every 5 minutes over a 60 minute testing session, using the MacLab computer software system (ADInstruments, Castle Hill, NSW, Australia) for the Macintosh microcomputer. The raw data were entered into a Microsoft Excel spread sheet, transferred to a statView spreadsheet, analyzed by 2-way ANOVA with post-hoc Scheffé tests with SAS StatView-V programs, and displayed as dose-effect plots with Cricket Graph software. All of the doses of d-threo-MPH, cocaine, and apomorphine tested increased locomotion markedly, from a saline basal level of 0.122±0.007 activity units/hour to 0.692±0.077 (5.68-fold increase), 1.25±0.07 (10.3 fold increase), and 1.18±0.08 (9.78-fold increase) units/hour, respectively. l-threo-MPH inhibited all three of these stimulants. The dose response curves of l-threo-MPH inhibition of locomotion in rats stimulated by d-threo-MPH, cocaine, or apomorphine are shown in FIGS. 2, 3, and 4, respectively. The potency of l-threo-MPH ($ID_{50}$) calculated from these graphs is approximately 2.5, 2.0, or 2.5 mg/kg, respectively.

What is claimed is:

1. A method of effecting dopamine inhibition in a mammal, said method comprising administering to said mammal l-threo-MPH which is substantially free from d-threo-MPH.

2. The method of claim 1, wherein said method is used for the treatment or prevention of a manic disorder.

3. The method of claim 1, wherein said method is used for the treatment or prevention of a psychotic disorder.

4. The method of claim 1, wherein said method is used for the treatment or prevention of an anxiety disorder.

5. A method of inhibiting the effects of a stimulant in a mammal, said method comprising administering to said mammal l-threo-MPH which is substantially free from d-threo-MPH.

6. The method of claim 5, wherein said stimulant is cocaine.

7. The method of claim 5, wherein said stimulant is an amphetamine.

8. The method of claim 5, wherein said stimulant is methcathinone.

9. The method of claim 5, wherein said stimulant is caffeine.

10. The method of claim 5, said method comprising treating or preventing the toxic effects of an overdose of said stimulant.

11. The method of claim 1, wherein l-threo-MPH is administered orally, intramuscularly, intravenously, or subcutaneously to said mammal.

12. The method of claim 11, wherein l-threo-MPH is administered together with a pharmaceutically acceptable carrier.

* * * * *

UNITED STATES PATENT AND TRADEMARK OFFICE
CERTIFICATE OF CORRECTION

PATENT NO. : 6,221,883 B1
DATED : April 24, 2001
INVENTOR(S) : Ross Baldessarini and Alexander Campbell It is certified that error appears in the above-identified patent and that said Letters Patent is hereby corrected as shown below:

Column 1,
Line 29, replace "residues" with -- resides --;
Line 54, replace "[$^{11}$C]d-threo" with -- [$^{11}$C]l-threo --;

Column 2,
Line 24, replace "rates" with -- rats --;
Line 24, replace "N=6/dos" with -- N=6/dose --;
Line 51, replace "dos-dependent" with -- dose-dependent --;

Column 3,
Line 13, replace "timulant" with -- stimulant --;

Column 19,
Line 19, replace "closure" with -- enclosure --.

Signed and Sealed this

Second Day of April, 2002

Attest:

JAMES E. ROGAN
Attesting Officer     Director of the United States Patent and Trademark Office